United States Patent [19]

Fischell

[11] Patent Number: 4,525,165
[45] Date of Patent: Jun. 25, 1985

[54] FLUID HANDLING SYSTEM FOR MEDICATION INFUSION SYSTEM

[75] Inventor: Robert E. Fischell, Silver Spring, Md.

[73] Assignee: The Johns Hopkins University, Baltimore, Md.

[21] Appl. No.: 439,138

[22] Filed: Nov. 4, 1982

Related U.S. Application Data

[63] Continuation-in-part of Ser. No. 34,155, Apr. 27, 1979, Pat. No. 4,373,527.

[51] Int. Cl.³ ............................................. A61M 7/00
[52] U.S. Cl. .................................. 604/131; 604/891; 128/DIG. 12
[58] Field of Search ............ 604/890, 891, 141, 48–49, 604/4, 65–66, 131; 128/DIG. 12–DIG. 13

[56] References Cited

U.S. PATENT DOCUMENTS

| | | | |
|---|---|---|---|
| 3,252,623 | 5/1966 | Corbin et al. | 604/65 X |
| 3,986,956 | 6/1976 | Anno | 604/65 X |
| 4,003,379 | 1/1977 | Ellinwood, Jr. | 604/49 X |
| 4,077,405 | 3/1978 | Hoerten et al. | 604/66 |
| 4,209,014 | 6/1980 | Sefton | 604/132 |
| 4,258,711 | 3/1981 | Tucker et al. | 604/131 X |
| 4,360,019 | 11/1982 | Portner et al. | 604/891 |

Primary Examiner—Kyle L. Howell
Assistant Examiner—Francis J. Jaworski
Attorney, Agent, or Firm—R. E. Archibald; H. W. Califano

[57] ABSTRACT

An apparatus for fluid handling and delivery in a medication infusion system is disclosed. The apparatus generally contains a pulsatile pump in combination with at least an accumulation flow restrictor. The pulsatile pump is economical in electrical consumption by virtue of the use of a spring force pumping action. The accumulator flow restrictor smooths the output from the pulsatile pump so that medication is delivered in a manner compatible with human or animal body needs. As an example, for infusion of medication such as insulin, the medication infusion system can provide an infusion flow profile which mimics that of insulin production in a normal person.

30 Claims, 10 Drawing Figures

FLUID HANDLING SYSTEM FOR MEDICATION INFUSION SYSTEM

CROSS REFERENCE TO RELATED APPLICATION

This is a continuation-in-part of patent application, Ser. No. 34,155, filed on Apr. 27, 1979, now U.S. Pat. No. 4,373,527.

BACKGROUND OF THE INVENTION

1. Field of the Invention

The present invention pertains to medication infusion systems, and more particularly to a fluid handling system for a medication infusion system.

2. Description of the Prior Art

The desirability of being able to infuse medication into a human or animal body has been recognized by prior and contemporary technology. Some such apparatuses are totally implantable while in others the pump and control apparatus is external to the living body and a catheter or the like is used to supply the medication to be infused into the living body. In either case delivering a medication flow which is controlled is imperative. Additionally, for infusion of medication such as insulin it is important that the infusion flow profile mimics that of insulin production in a normal person.

Another consideration, especially in implanted pumps, is that power consumption be kept to a minimum to insure adequate battery life.

To control the flow of medication from an infusion pump it has been suggested that a flow restrictor can be employed. Such flow restrictors are taught in U.S. Pat. Nos. 3,731,681, 3,894,538, 3,951,147 and 4,077,405. U.S. Pat. No. 4,299,220 teaches the use of a pressure regulation system in combination with a passive pump for infusing drugs.

The use of a fluid accumulator in combination with a fluid flow restrictor is taught in U.S. Pat. Nos. 4,192,397 and 4,221,219. Both of these patents employ a passive pump which operates under the principal of having pressure applied to a reservoir such that fluids stored within the reservoir is forced thereout. While such a pump configuration does not in and of itself require electrical consumption it basically is uncontrollable unless valves or the like are used to control flow from the pump.

The present invention solves the problems associated with the prior art by using a pulsatile pump in conjunction with an accumulator flow restrictor network to give the advantage of low power consumption since a pulsatile pump as taught herein is economical in electrical consumption by virtue of the use of spring force to pump and which also provides, in combination with the accumulator flow restrictor a delivery of medication which has a profile that is smoothed and therefore desirable for certain applications such as infusion of insulin.

A pulsatile pump is shown in the U.S. Pat. No. 4,152,098 but its use in combination with an accumulator flow restrictor is not shown or suggested.

SUMMARY OF THE INVENTION

Therefore, a primary object of the present invention is to provide an infusion apparatus for providing medication to a living body of a patient which can be configured to have a smooth flow of medication for infusion.

A further object of the present invention is to provide an infusion apparatus for providing medication to a living body of a patient which has minimal electrical consumption so that the longevity of its power source is maximized.

A still further object of the present invention is to provide an infusion apparatus for providing medication to the living body of a patient which mimics the natural flow profiles of body produced substances such as insulin or reproductive sex hormones.

Still another object of the present invention is to provide greater flow smoothing at slow medication delivery rates while still allowing faster delivery rates when that is required.

Still another object of the present invention is to provide an infusion apparatus for providing medication to the living body of a patient which can be practiced with sufficient design flexibility to permit the crucial components thereof to be incorporated either in the main housing thereof or in the catheter thereof used to deliver the medication to the living body.

Still another object of the present invention is to provide an infusion apparatus for providing medication to a living body of a patient which permits exquisitely precise control of medication dosing.

Still another object of the present invention is to provide medication flow rates which are not altered by normal variations in barometric pressure or pressure variations occurring from a rapid change in the patient's altitude.

Still another object of the present invention is to provide an infusion apparatus for providing medication to a living body.

These objects, as well as further objects and advantages of the present invention will become readily apparent after reading the ensuing description of a non-limiting illustrative embodiment and viewing the accompanying drawings. An infusion apparatus for providing medication to a living body of a patient according to the principles of the present invention, comprises: a medication reservoir for storing selected medication; means for pumping said selected medication, said pump means operating in a pulsatile mode capable of producing a pulsing output flow, the input of said pump means being in communication with said reservoir; means for accumulating said selected medication, the input of said accumulator means being in communication with the output of said pump means; means for restricting the flow of said selected medication, the input of said flow restrictor means being in communication with the output of said accumulator means, said flow restrictor in combination with said accumulator means smoothing the pulsatile nature of the flow of said selected medication; and means for communicating said selected medication from the output of said flow restrictor means to said living body possibly through a catheter connected to the output of the said flow restrictor. The present invention also provides for additional accumulator flow restrictor combinations to be put in series with a first accumulator flow restrictor assembly to further enhance the smoothing characteristics of the apparatus if desired.

BRIEF DESCRIPTION OF THE DRAWING

In order that the present invention may be more fully understood, it will now be described, by way of example, with reference to the accompanying drawings in which.

DESCRIPTION OF THE PREFERRED EMBODIMENTS

Figure 1:
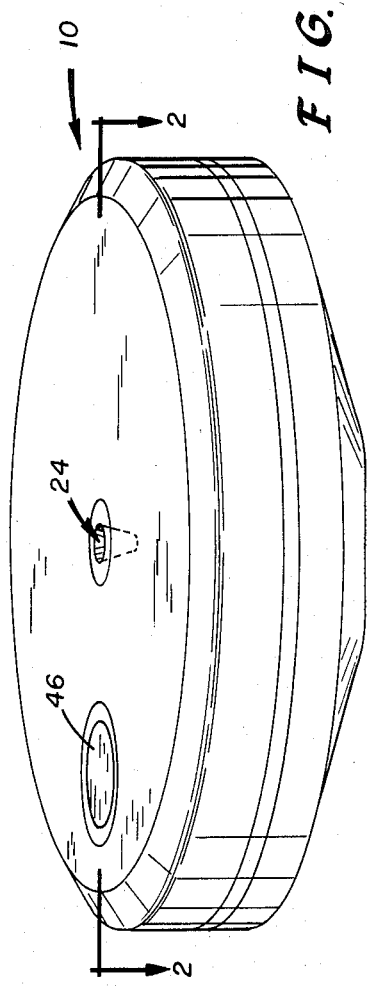
FIG. 1 is a prospective view of an implantable infusion apparatus constructed in accordance with the principles of the present invention.
Figure 2:
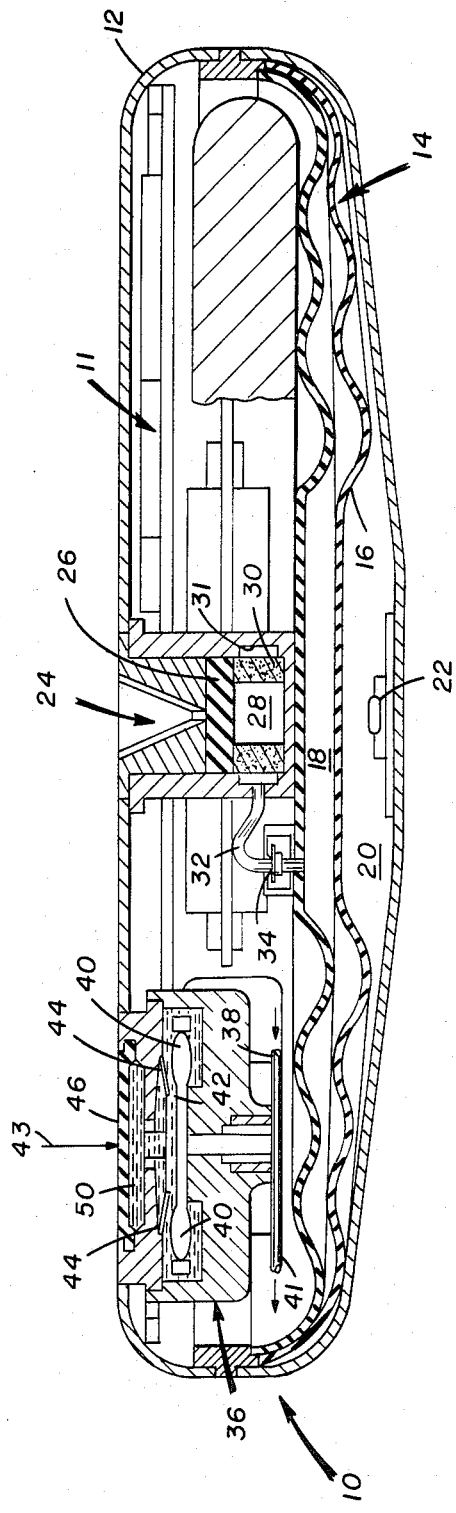
FIG. 2 is a cross-sectional view of the apparatus of FIG. 1.

For purposes of illustration the present invention will be described as employed in an implantable infusion apparatus. However, it is to be understood that the teachings herein can also be applied to an apparatus where some or all of the components thereof are situated such that they are external to a living body. Referring now to the figures, and more particularly to FIGS. 1 and 2 thereof, there is illustrated therein an implantable infusion apparatus 10. The infusion apparatus 10 is configured for implantation inside a living body and includes a housing 12 formed of a biocompatible material such as titanium or the like and which includes control electronics shown generally at 11, in locations as generally disclosed in the parent patent. The housing 12 incorporates a medication reservoir section 14 which includes a flexible diaphragm 16 that divides the medication reservoir section 14 into a medication chamber 18 and a liquid-vapor chamber 20. The medication chamber 18 is for storage of the medication to be infused into the living body and the liquid-vapor chamber 20 is filled with a saturated vapor and some liquid of a fluorocarbon such as Freon 113 or some other appropriate pressurant. Over normal body temperatures, Freon 113 can readily change from a liquid to vapor and visa versa and therefore, at the essentially constant temperature of the human body it will maintain the liquid-vapor chamber 20 and therefore the medication chamber 18 at an essentially fixed pressure regardless of the amount of medication disposed within the medication chamber 18.

Figure 4:
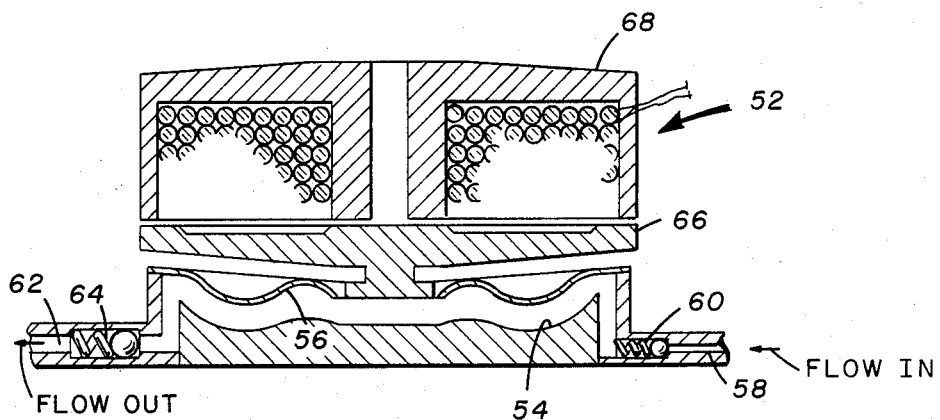
FIG. 4 is a cross-sectional view in elevation of a pump incorporating the principles of the present invention.

As the medication chamber 18 is filled with medication, as hereinafter described, the flexible diaphragm 16 distends downward (with reference to the Figure) toward the bottom of the housing 12 and, eventually comes in contact with a limit switch 22 which senses that the medication chamber 18 has reached a preselected degree of fullness. As medication is drawn from the medication chamber 18 by a pulsatile pump 52 (not shown in FIG. 2) which is illustrated in FIG. 4, the flexible diaphragm 16 moves upward from the base of the housing 12. Filling of the medication chamber 18 is accomplished through a fill port 24 closed by a self-sealing septum 26. A needle is inserted through the fill port 24 and through the septum 26 so that it can communicate fluid to an antechamber 28. The antechamber 28 is provided with a filter 30 for filtering the medication after which the medication is collected in a manifold 31 and the medication then passes through a conduit 32 and a one-way check valve 34 after which it enters the medication chamber 18.

Figure 3:
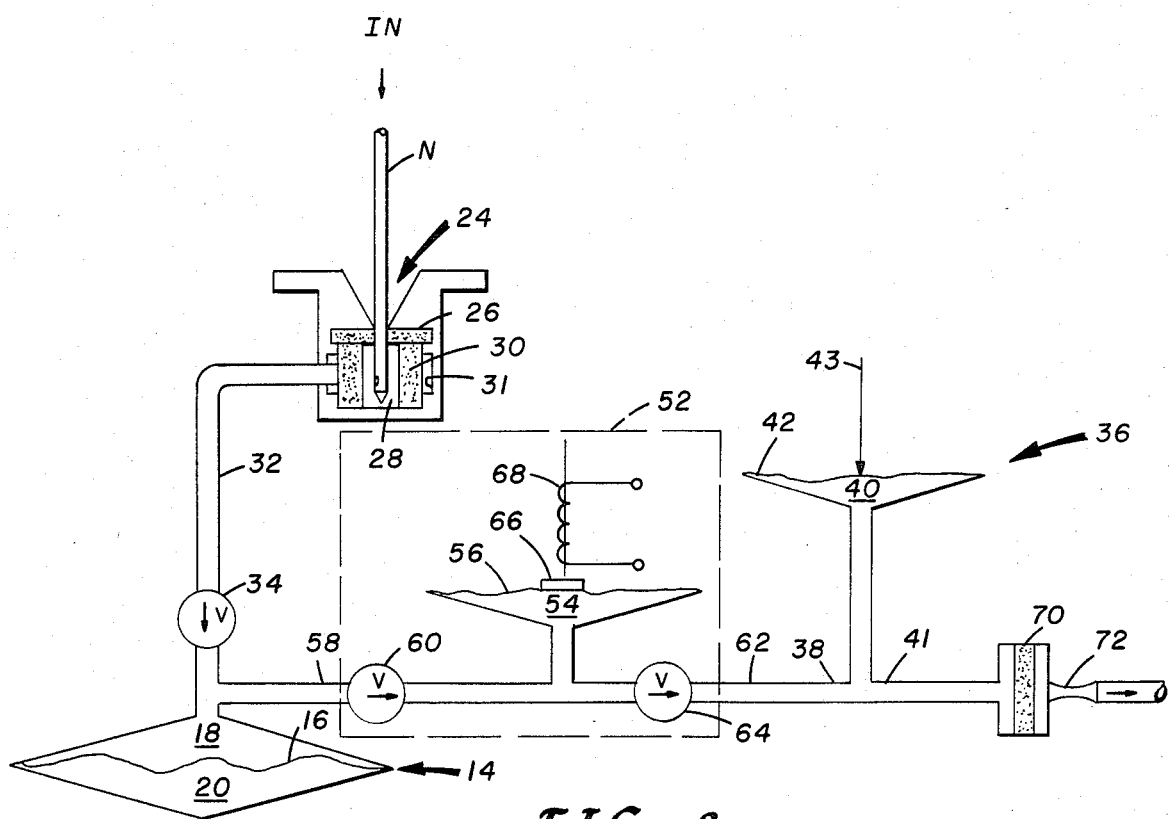
FIG. 3 is a schematic drawing of the apparatus of the present invention.

Medication is drawn from the medication chamber 18 by the pulsatile pump 52 illustrated schematically in FIG. 3, and further in FIG. 4 and still further described in conjunction therewith and then is delivered to an accumulator 36. The flow from the pulsatile pump is delivered to the accumulator 36 through an input 38. Fluid leaves the accumulator 36 from an output 41 and then travels to a flow restrictor further illustrated in FIG. 3. The accumulator 36 forms a variable volume chamber 40 therein. The variable volume chamber 40 includes flexible walls 42 which move outwardly as the variable volume chamber is filled. The variable volume chamber 40 returns to a preselected minimum volume when at rest, and, after expansion returns to such a minimum volume due to a force having a spring constant determined by the characteristics of the flexible walls 42. Because of the design of the present invention, the accumulator 36 returns to its initial minimum volume due to a force having a spring constant dictated by the flexible walls 42 and/or a second spring constant dictated by a plurality of leaf springs 44. The leaf springs 44 are positioned adjacent to the upper flexible wall 42 such that when a preselected degree of expansion of the wall 42 has taken place the wall 42 comes in contact with the leaf springs 44. The spring constant of the leaf springs 44 is greater than the spring constant of the flexible walls 42. As a result, when the variable volume chamber 40 is filled to a volume such that the flexible wall 42 does not touch the leaf springs 44 the accumulator 36 has one spring constant. When the variable volume chamber 40 is filled and expands such that the flexible wall 42 comes in contact with and is under the influence of the leaf springs 44 the accumulator 36 has another spring constant which is higher. The output 41 of the accumulator 36 is in communication with a flow restrictor, as hereinafter described. The accumulator flow restrictor combination has two different time constants, the first one of which is longer for small volumetric displacements of the variable volume chamber 40 and another which is shorter for larger volumetric displacements of the variable volume chamber 40. The shorter time constant occurring after the upper flexible wall 42 has come in contact with the leaf springs 44.

Figure 5:
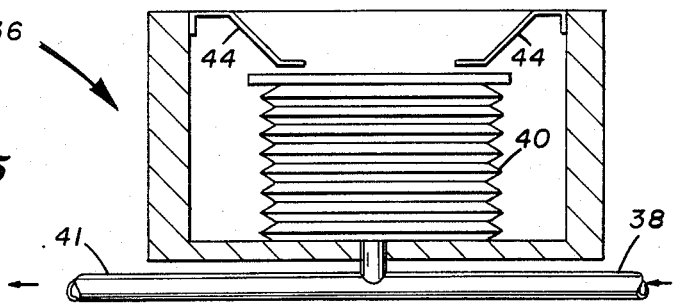
FIG. 5 is a schematic view of an accumulator incorporating the principles of the present invention.

Of course, it is to be understood that the different spring constants necessary for the functioning of the accumulator 36 can be provided thereto in manners other than the inherent flexibility of the walls 42 and the use of the leaf springs 44. For instance, FIG. 5 illustrates an accumulator in which the variable volume chamber 40 is a bellows having a first spring constant and as the bellows expands it contacts leaf springs 44 which supply a second higher spring constant. Other spring arrangements can be employed so long as a differential between two spring rates is provided. It is also within the contemplation of this invention that a multiplicity of spring rates associated with different volume levels in the variable volume chamber can be used to provide various degrees and methods of fluid flow smoothing.

Since the ambient pressure to which a living body is subject can vary in the course of a day because of normal barometric changes as well as travel in an elevator, a pressurized airplane cabin, or travel to different altitudes it is possible that the fluid flow out of a dual-rate accumulator as above described could be effected by such pressure changes. In order for the fluid delivery rate to be impervious to sudden or gradual changes in ambient pressure, it is desirable to reference the flexible wall 42 of the accumulator to ambient body pressure. This is accomplished by the provision of a flexible membrane 46 mounted on the housing 12, the membrane 46 being exposed to the ambient pressure 43 of the living body. Behind the flexible member 46 is a fluid chamber 48 filled with a suitable fluid 50. The fluid 50 fills the fluid chamber 48 and also contacts the exterior of the flexible walls 42 so that the flexible walls are referenced to body pressure 43 through transmission of pressure from the living body through the flexible membrane 46 and the fluid 50 to the flexible walls 42.

With reference to FIG. 3, the overall operation of the system can be understood. Beginning at the fill port 24 the sharp end of a non-coring hypodermic needle is shown inserted through the septum 26 and into the antechamber 28 so that a desired medication can be passed through the filter 30, into the manifold 31 and thence to the medication reservoir 14 by way of the check valve 34. Medication flows from the output of the medication chamber 18 when drawn therefrom by a pulsatile pump 52 further illustrated in FIG. 4. The pulsatile pump 52 includes a bellows chamber 54 which varies in volume as a result of the motion of the flexible wall 56 that is connected to a magnetizable armature 66 that is driven by the permeable core coil 68. The bellows chamber 54 is connected on the input 58 thereof to the medication chamber 18 through a one-way valve 60. The output 62 of the pump 52 is connected to the bellows chamber 54 through a one-way valve 64. One-way valves 60 and 64 are of the ball and spring type and operate such that an increase in volume of the bellows chamber 54 causes opening of the valve 60 so that medication can be drawn therein. A decrease in the volume of the bellows chamber 54 causes the closing of valve 60 and the opening of valve 64 so that medication can be delivered to the input 38 of the accumulator 36.

The volume of the bellows chamber 54 is varied by the flexing of the flexible wall 56, this flexing being accomplished by the drawing of a magnetizable armature 66 toward a permeable core coil 68 and the returning of the armature 66 to a rest position as a result of the inherent spring constant of the flexible wall 56 which could be supplemented by additional leaf springs or other types of springs. Therefore, when at rest, the bellows chamber 54 is at a minimum volume and when the permeable core coil 68 is energized the magnetizable armature 66 is drawn adjacent thereto to put the bellows chamber 54 at a maximum volume. When the coil 68 is de-energized, the magnetizable armature 66, by virtue of the inherent spring constant of the flexible wall 56 returns to its rest position and the bellows chamber 54 returns to minimum volume. The maximum volume which the bellows chamber 54 can assume is limited by the maximum travel of the armature 66 and, as illustrated this is accomplished through the fixed relative position of the armature 66 to the flexible wall 56 and the abutment of the armature 66 against the surface of the permeable core of the coil 68.

A preferred embodiment for the flexible wall 56 is a convoluted diaphragm which is rigidly mounted at its edges and is therefore a movable section that is in contact with the medication disposed in the bellows chamber 54. The flexible wall 56 is inhibited from moving when the pressure P in the bellows chamber means exceeds the spring force F of the flexible wall 56 divided by the effective area of the surface of the flexible wall in contact with the selected medication, i.e., when $P_{max} = F/A$. Effective area is defined as the projected area of a portion of the flexible wall in contact with the selected medication and which moves such that it is perpendicular to the spring force of the flexible wall 56. In more general terms, effective area will be the surface area in contact with the medication which is perpendicular to the spring force of the variable volume.

Should a malfunction occur in the electronics and a continuous sequence of rapid pulses be introduced to the permeable core coil 68, causing the armature 66 to reciprocate, the return of the flexible wall 56 to its orginal position would be inhibited once the pressure in the bellows chamber 54 exceeds $P_{max}$. The pressure builds up rapidly because of the flow restrictor 72. Therefore, the possibility of introducing drugs or other medication at a high rate, which would be unsafe for the patient, is essentially eliminated.

The pump 52 pumps a fixed volume of fluid each time the coil 68 is energized because of constraint on the movement of the armature 66. Once the electrical pulse current with the coil exceeds a certain value, the stroke volume of the pump 52 is constant and independent of any increase in the electrical pulse current or pulse width or pulse energy into the coil 68. Therefore a known dosage of medication is released with each pulse as long as a certain minimum value of pulse current is exceeded.

In designing the pump, one could select a nominal pulse current that is twice the value needed to maintain a constant stroke volume. This then would assure the constant volume per stroke even if the pulse current fell to $\frac{1}{2}$ its nominal value.

The medication reservoir 14 is preferably maintained at a pressure level below the internal pressure of the living body and this characteristic will not have an effect on the pressure within the pump since the pump pressure is independently generated by the spring force of the flexible wall 56. As the medication leaves the pump output 62 it enters the input 38 of the accumulator 36 and flows into the variable volume chamber 40 thereof as illustrated both in FIG. 2 and FIG. 3. Upon expansion of the variable volume chamber 40 the flexible wall 42 is subject to a spring force 43, and such spring force may have a single spring constant, or it may have two spring constants for different volumetric expansions of the variable volume chamber 40 (illustrated in FIG. 5), or it may have two spring constants and also be responsive to the ambient atmospheric pressure 43 (illustrated in FIG. 2). Flow from the accumulator 36 leaves the output 41 thereof and enters a filter 70. The filter 70 is provided to preclude debris in the medication from clogging a flow restrictor 72 when the medication is supplied thereto. The flow restrictor 72 is essentially a length of tube in which a portion of the internal diameter thereof sized to partially restrict the flow of medication therethrough. Alternately, the filter 70 can act by itself as a flow restrictor and can be used alone or in combination with a constricted tube. Additionally, other means of restricting liquid flow are well known to any person of ordinary skill in the fluid systems art.

Figure 6:
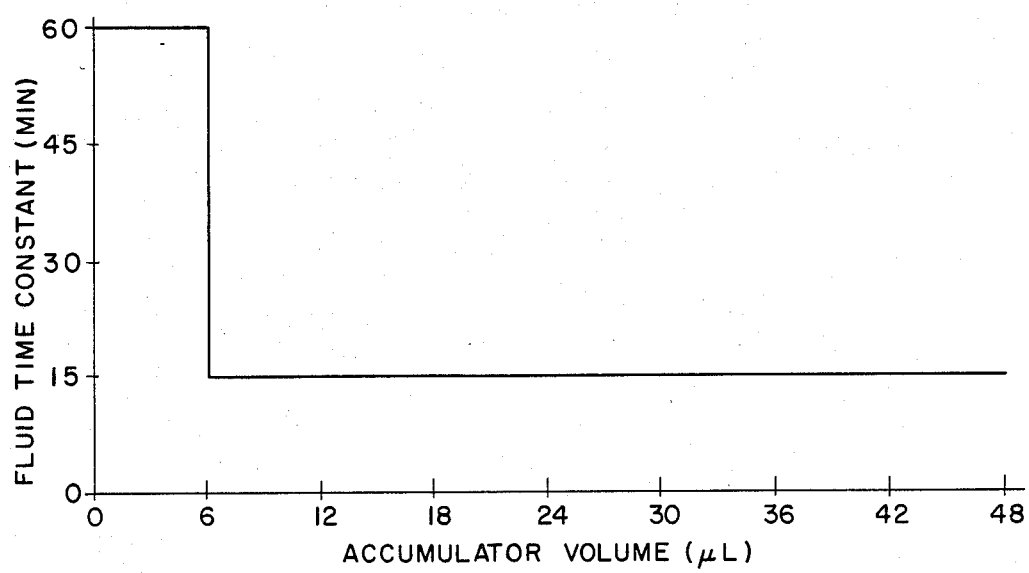
FIG. 6 illustrates the behavior of an accumulator showing fluid time constant versus accumulator volume in an accumulator constructed in accordance with the principles of the present invention.

By use of an accumulator having two different time constants in conjunction with a suitably sized flow restrictor, the pulsatile flow of medication leaving the pump 52 is smoothed. The accumulator acts in a manner analogous to an electrical capacitor and the flow restrictor acts in a manner analogous to an electrical resistor, the two working together to create an RC time constant which results in this smoothing. To satisfactorily mimic the natural delivery of certain substances such as insulin to a living body, it is desirable to deliver the medication rather smoothly as compared to pulsatile delivery. When the pulsatile pump 52 pumps at very slow rates, a long time constant is needed to smooth the flow. When pumping takes place at a rapid rate a long time constant is no longer desired and a short time constant is desired to obtain rapid flow of medication. The design of the present accumulator provides long time constants for small displacements and shorter time constants for greater displacement of the variable volume chamber 40. With reference to FIG. 6, this performance characteristic is shown. As an example, for the accumulator characteristic illustrated at stored volumes of six microliters or less the time constant in the accumulator when combined with the flow restrictor is 60 minutes. For stored volumes between 6 and 48 microliters, the time constant of the accumulator is reduced to 15 minutes.

Figure 7:
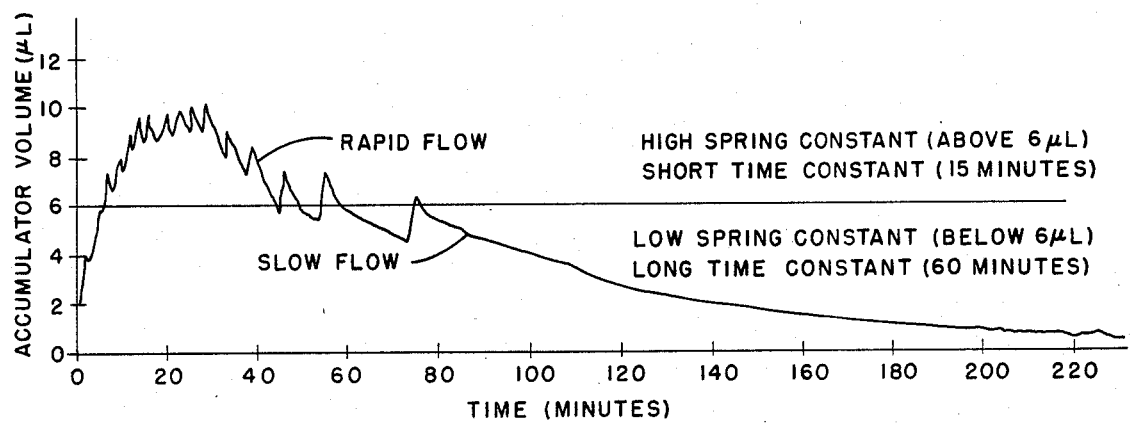
FIG. 7 is a graph of accumulator volume versus time for an accumulator constructed with the principles of the present invention.

FIG. 7 shows the stored volume in the accumulator plotted against time, the accumulator providing two different time constants depending on accumulator volume as shown in FIG. 6. In FIG. 7, at low volumes of the accumulator (below 6 $\mu$L), the accumulator is subject to a lower spring constant which results in a slow drug flow. However, when one exceeds a stored volume of 6 microliters, for this particular accumulator, the spring constant increases; the time constant immediately becomes shorter, and the medication is delivered at a faster rate. By this construction, it is possible to provide a smooth basal flow rate of medication while at the same time providing for a comparatively high rate of flow when desired to infuse supplemental medication (for example, insulin immediately after eating).

Figure 8:
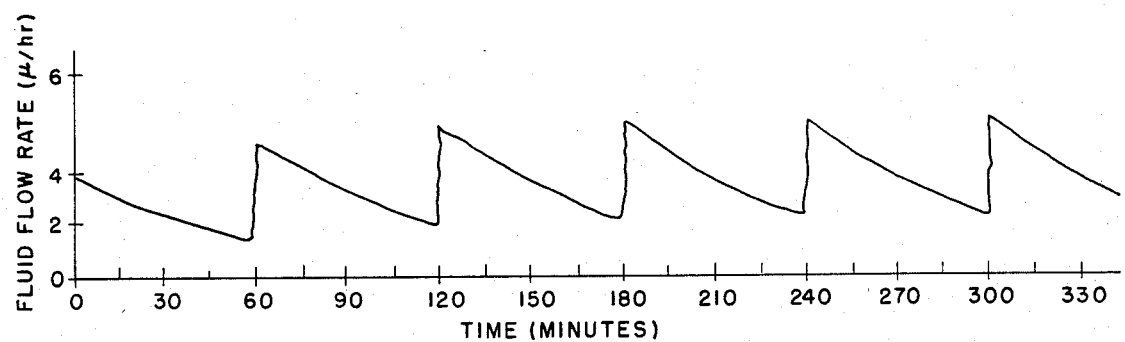
FIG. 8 is a graph of the fluid flow rate out of an accumulator flow resistor combination constructed in accordance with the principles of the present invention.

FIG. 8 shows flow rate out of the flow restrictor as a function of time for an accumulator flow restrictor combination wherein a single accumulator and single flow restrictor is employed. In FIG. 8, the accumulator remains at low volumetric displacement and the time constant therefore does not shift. It can be seen that the medication flow rate profile has been smoothed by the accumulator flow restrictor combination.

Figure 9:
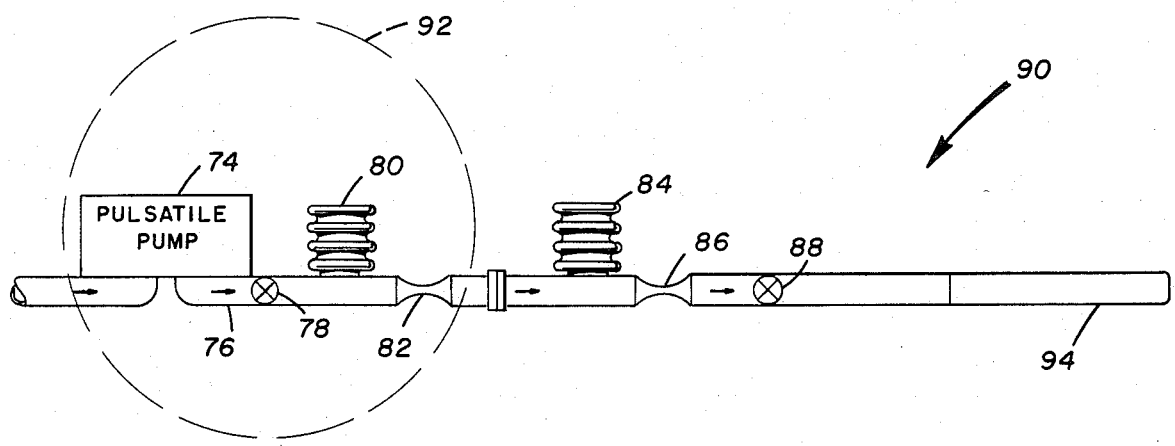
FIG. 9 is a schematic representation of an infusion apparatus incorporating dual accumulator-flow restrictor assemblies one of which assemblies is integral with a fluid catheter.

It has been found that employment of a second accumulator and flow restrictor in series with the first one achieves an increased smoothing of the flow of medication. With reference to FIG. 9 there is illustrated therein an alternate embodiment of the present invention which employs a pulsatile pump 74 having the output 76 thereof coupled to a valve 78 and then to a first accumulator 80. The accumulator in turn is in communication with a flow restrictor 82 and the output of the flow restrictor 82 is in communication with a second accumulator 84. The output of the second accumulator 84 is in communication with a second flow restrictor 86. The output of the second flow restrictor 86 flows through a check valve 88 and into the end of a catheter 90 as illustrated. The first accumulator 80 and first flow restrictor 82 are disposed within a housing 92 and the second accumulator 84 and second flow restrictor 86 are disposed within a catheter 90. While this has been shown for matter of convenience it is to be understood that the multiple flow restrictors and accumulators may be entirely disposed within the housing 92 or can be disposed entirely in the catheter 90. This is also the case with a configuration employing a single accumulator and a single flow restrictor such that either, (1) both the accumulator and the flow restrictor can be disposed within the housing, or (2) the accumulator can be disposed within the housing and the flow restrictor within the catheter or, (3) both the accumulator and flow restrictor can be in the catheter. The catheter 90 is also illustrated with a pyrolytic carbon tip 94 a material known to be the least thrombogenic of any known material. Check valve 88 is provided to ensure that body fluids cannot flow into the infusion apparatus. The use of such a check valve and the pyrolytic carbon tip is also applicable to a single accumulator flow restrictor configuration. The accumulators 80 and 84 function in the same manner as the accumulator 36 hereinbefore described, and both can include one or two spring rates to provide one or two time constants in conjunction with their associated rstrictors 82 and 86.

Figure 10:
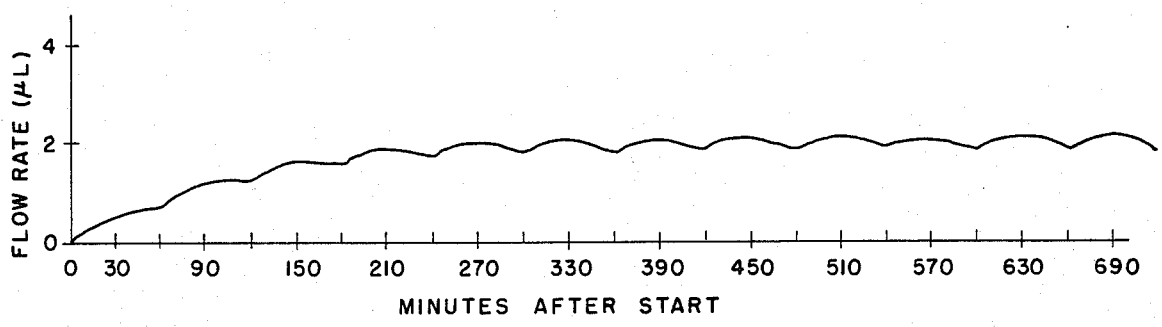
FIG. 10 is a graph of the flow rate characteristics of the apparatus of FIG. 9.

With reference to FIG. 10, the performance characteristics of the system of FIG. 9 are illustrated where the flow rate has been graphed against time. This flow is even smoother as compared to that which is achievable with a single accumulator, flow restrictor as previously discussed in conjunction with FIG. 8.

It should be apparent that additional accumulator flow restrictors can be used in series with the two accumulator flow restrictors previously discussed to provide even more dramatic smoothing when desirable, i.e., when a medication will only be effective when administered at a very smooth and controlled rate. Although specific accumulator volumes and flow rates have been illustrated it is to be understood that these are for purposes of showing the principles of the present invention and are not to be limiting to the manner in which these principles can be applied to a broad range of differently configured and sized accumulators and flow restrictors. Furthermore it will be understood that various changes in the details, materials, arrangements of parts and operational conditions which have been herein described and illustrated in order to explain the nature of the invention may be made by those skilled in the art within the principles and scope of the present invention.

Having thus set forth the nature of the invention, what is claimed is:

1. An infusion apparatus for providing medication to a living body of a patient comprising:
a medication reservoir for storing selected medication;
means for pumping said selected medication responsive to actuating commands for pumping fixed volume pulses at a variable rate, said pump means operating in a pulsatile mode, the input of said pump means being in communication with said reservoir;
means for actuating said pump means at a variable rate;
means for accumulating said selected medication, said means for accumulating comprising a variable volume chamber, the input of said accumulator means being in communication with the output of said pump means whereby said accumulator means may be filled at a variable rate governed by said pump means;

means for restricting the flow of said selected medication, the input of said flow restrictor means being in communication with the output of said accumulator means, said flow restricator means in combination with said accumulator means smoothing the pulsatile nature of the flow of said selected medication; and means for communicating said selected medication from the output of said flow restrictor means to said living body.

2. An apparatus in accordance with claim 1, wherein said variable volume chamber includes means for providing a deformation force for returning said chamber to a preselected minimum volume when at rest, filling of said variable volume chamber causing the expansion thereof.

3. An infusion apparatus in accordance with claim 1, wherein said variable volume chamber includes means for providing a deformation force for returning said chamber to a preselected minimum volume when at rest, filling of said variable volume causing the expansion thereof, said deformation means having a first spring constant during a first selected range of volumes and a second spring constant during a second selected range of volumes.

4. An infusion apparatus in accordance with claim 3, wherein said first spring constant is smaller than said second spring constant, said first selected range of volume being smaller than said second selected range of volume, said accumulator means in combination with said flow restrictor means therefore having a time constant which is longer for said first selected range of volumes than the time constant for said second selected range of volumes.

5. An infusion apparatus in accordance with claim 4, wherein said accumulator means comprises at least one flexible wall having an inherent spring constant as said deformation means having a first spring constant; and, spring means mounted adjacent to said flexible wall as said deformation means having a second spring constant such that a preselected amount of flexing of said wall upon filling of said variable volume chamber causes contact of said flexible wall with said spring means, said spring means having a spring constant higher than said inherent spring constant of said flexible wall, said flexible wall effectively having a greater spring constant when in contact with said spring means.

6. An infusion apparatus in accordance with claim 5, further comprising means for referring said flexible wall to the ambient pressure of said living body.

7. An infusion apparatus in accordance with claim 1, further comprising a second accumulator-flow restrictor assembly including another means for accumulating said selected medication and another means for restricting the flow of said selected medication, the output of said another accumulator means being in communication with the input of said another flow restrictor means, said another flow restrictor in combination with said another accumulator means smoothing the pulsatile nature of the flow of said selected medication as a result of said at least one accumulator-flow restrictor assembly being interposed between the said restrictor means and said communication means, the input of said another accumulator means being in communication with said output of said restrictor means, said communication means communicating said selected medication from the output of said another flow restrictor means to said living body.

8. An infusion apparatus in accordance with claim 7, wherein both said accumulator means each comprise a variable volume chamber including means for providing a deformation force for returning said chambers to a preselected minimum volume when at rest, filling of said variable volume chamber causing the expansion thereof, said deformation force means having a first spring constant during a first selected range of volumes and a second spring constant during a second selected range of volumes.

9. An infusion apparatus in accordance with claim 8, wherein said first spring constant of said accumulator means is smaller than the second spring constant of said accumulator means, and the first spring constant of said another accumulator means is smaller than the second spring constant of said another accumulator means, said first selected range of volumes of said accumulator means being smaller than said second selected range of volumes of said accumulator means, said first selected range of volumes of said another accumulator means being smaller than said second selected range of volumes of said another accumulator means, each of said accumulator means in combination with the associated said flow restrictor means having a time constant which is longer for volumetric displacements in each of said first selected ranges of volumes than the time constant for volumetric displacements in each of said second selected ranges of volumes.

10. An infusion apparatus in accordance with claim 9, further comprising means for referencing at least one of said accumulator means to the ambient pressure of said living body.

11. An infusion apparatus in accordance with claim 1, wherein said pump means comprises a bellows chamber means for storing said selected medication within said pump means, an increase in volume of said bellows chamber means permitting drawing of said selected medication through said input of said pump means into said bellows chamber means, a decrease in volume of said bellows chamber means permitting expulsion of said selected medication out of said bellows chamber means through said output of said pump means.

12. An infusion apparatus in accordance with claim 11, further comprising an input pressure valve and an output pressure valve, each of said pressure valves being normally closed, said input pressure valve being disposed between said pump means input and said bellows chamber means, an increase in volume of said bellows chamber means causing said input pressure valve to open and said selected medication to enter said bellows chamber means, a decrease in volume of said bellows chamber means causing said output pressure valve to open and said input pressure valve to close, so as to permit said selected medication to enter said input of said accumulator means as a pressure pulse.

13. An infusion apparatus in accordance with claim 12, wherein said bellows chamber means comprises at least one flexible wall, movement of said flexible wall varying the volume of said bellows chamber means, and means for moving said flexible wall.

14. An infusion apparatus in accordance with claim 13, further comprising spring means for urging said flexible wall in a manner which decreases the volume of said bellows chamber means, the magnitude of the force applied to and stored by said spring means increasing as the volume of said bellows chamber means increases due to the displacement of said flexible wall thereof by said moving means.

15. An infusion apparatus in accordance with claim 14, wherein said flexible wall serves as said spring means.

16. An infusion apparatus in accordance with claim 15, wherein said flexible wall has a surface in contact with said selected medication which can be drawn into said bellows chamber means.

17. An infusion apparatus in accordance with claim 16, wherein said flexible wall is attached to a magnetizable plate, said moving means comprising a coil disposed proximate to said plate, said coil selectively causing a pulsing magnetic field, pulsing of said coil causing said plate to be moved.

18. An infusion apparatus in accordance with claim 17, wherein said flexible wall of said bellows chamber means is inhibited from moving when the pressure (P) in said bellows chamber means exceeds the spring force (F) of said flexible wall divided by the effective area (A) of said surface of said flexible wall in contact with said selected medication, that is when $P_{max}=F/A$ and wherein said restricting means will then limit the flow to a selected maximum level when said coil is pulsed too rapidly, thereby providing a safety feature.

19. An infusion apparatus in accordance with claim 17, wherein said plate comprises a magnetizable magnetic armature.

20. An infusion apparatus in accordance with claim 15, further comprising means for limiting the distance said plate can move in both a volume increasing direction and a volume decreasing direction.

21. An infusion apparatus in accordance with claim 1, further comprising means for maintaining the pressure within said medication reservoir at a pressure level below the internal pressure of said living body.

22. An infusion apparatus in accordance with claim 21, wherein said pressure maintaining means comprises:
a flexible diaphragm which divides said medication reservoir into a medication chamber and a liquid-vapor pool chamber; and
a liquid vapor pool disposed within said liquid-vapor pool chamber, the proportion of liquid to vapor in said liquid-vapor pool varying in response to variations in the amount of said selected medication disposed in said medication chamber.

23. An infusion apparatus in accordance with claim 1, wherein said restrictor means comprises a length of tubing which has a portion of the internal diameter thereof sized to partially restrict the flow of said medication therethrough.

24. An infusion apparatus in accordance with claim 1, wherein said restrictor means comprises a filter of the type which partially restricts flow therethrough.

25. An infusion apparatus in accordance with claim 1, wherein said communication means comprises a catheter.

26. An infusion apparatus in accordance with claim 25, wherein said catheter has the tip thereof formed of pyrolytic carbon.

27. An infusion apparatus in accordance with claim 26, further comprising a check valve means disposed in said catheter, said check valve means permitting the flow of said selected medication out of said catheter but precluding the flow of body fluid of said living body from flowing therein.

28. An infusion apparatus in accordance with claim 1, further comprising a filter operably interposed between said accumulator means and said flow restrictor means to preclude the obstruction of said flow restrictor means.

29. An infusion apparatus in accordance with claim 1, further comprising a housing for containing said pump means, said accumulator means, and said restrictor means, said housing being biocompatible and for implantation within said living body.

30. An infusion apparatus for providing medication to a living body of a patient comprising:
a medication reservoir for storing selected medication;
means for pumping said selected medication, said pump means operating in a pulsatile mode, the input of said pump means being in communication with said reservoir wherein said pump means comprises,
a variable volume bellows chamber having an input and output, said input being in communication with said medication reservoir, said variable volume chamber having an effective area (A),
a moving means which is activated for increasing the volume of said bellows chamber to a preselected maximum volume thereby drawing said selected medication from said medication reservoir,
a spring means for urging said bellows chamber to contract to a preselected minimum volume, thereby forcing said selected medication through said output, said spring means providing a spring force (F), whereby said spring means is unable to force said selected medication through said output when the pressure (P) in said bellows chamber exceeds said spring force (F) divided by said effective area (A), that is when, $P_{max}=F/A$;
means for restricting the flow of said selected medication, the input of said flow restrictor means being in communication with said output of said pump means, wherein said restricting means will restrict the maximum medication flow rate into said living body, and said maximum flow rate is obtained when the pressure in said bellows chamber reaches $P_{max}$ which is a result of said moving means being activated at a rapid rate, thereby preventing said pumping means from providing said selected medication at an unsafe dosage; and
means for communicating said selected medication from the output of said flow restrictor means to said living body.

* * * * *